US009332965B2

United States Patent
Lee et al.

(10) Patent No.: US 9,332,965 B2
(45) Date of Patent: May 10, 2016

(54) METHOD AND APPARATUS FOR MANAGING AND DISPLAYING ULTRASOUND IMAGE ACCORDING TO AN OBSERVATION OPERATION

(71) Applicant: SAMSUNG MEDISON CO., LTD., Gangwon-do (KR)

(72) Inventors: Sung-mo Lee, Gangwon-do (KR); Sung-yoon Kim, Gangwon-do (KR); Mi-jeoung Ahn, Gangwon-do (KR); Jun-kyo Lee, Gangwon-do (KR); Dong-gyu Hyun, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 252 days.

(21) Appl. No.: 13/971,482

(22) Filed: Aug. 20, 2013

(65) Prior Publication Data

US 2014/0050381 A1 Feb. 20, 2014

(30) Foreign Application Priority Data

Aug. 20, 2012 (KR) ........................ 10-2012-0090898

(51) Int. Cl.
*G06K 9/00* (2006.01)
*A61B 8/08* (2006.01)
(Continued)

(52) U.S. Cl.
CPC ............... *A61B 8/5223* (2013.01); *A61B 8/463* (2013.01); *A61B 8/465* (2013.01); *A61B 8/483* (2013.01); *A61B 8/523* (2013.01); *A61B 8/5292* (2013.01); *G01S 7/52073* (2013.01); *G01S 7/52074* (2013.01); *G01S 15/8993* (2013.01);
(Continued)

(58) Field of Classification Search
None
See application file for complete search history.

(56) References Cited

U.S. PATENT DOCUMENTS

2005/0251036 A1* 11/2005 Abuhamad .................... 600/437
2007/0167704 A1* 7/2007 Chance ......................... 600/407
(Continued)

FOREIGN PATENT DOCUMENTS

| EP | 1 550 883 A2 | 7/2005 |
|---|---|---|
| EP | 2289418 A1 | 3/2011 |

(Continued)

OTHER PUBLICATIONS

Korean Notice of Final Rejection issued in corresponding Korean Patent Application No. 10-2012-0090898, mailed on Jan. 26, 2015; 6 pages with English translation.
(Continued)

*Primary Examiner* — Tahmina Ansari
(74) *Attorney, Agent, or Firm* — McDermott Will & Emery LLP

(57) ABSTRACT

A method of managing an ultrasound image, the method including storing a plurality of pieces of setting information to respectively match a plurality of observation operations for diagnosing an object, each of the plurality of pieces of setting information including at least one from among information about an observation plane that splits ultrasound volume data in a predetermined direction, information about a split method of splitting the ultrasound volume data, and information about a reference point; displaying a plurality of plane images for a current observation operation, wherein the plurality of plane images are obtained based on a piece of the setting information matching the current observation operation; storing an image selected from among the plurality of plane images according to an external input signal such that the selected image matches the current observation operation.

29 Claims, 10 Drawing Sheets

(51) Int. Cl.
*A61B 8/00* (2006.01)
*G01S 7/52* (2006.01)
*G01S 15/89* (2006.01)
*G06T 19/00* (2011.01)
*A61B 8/13* (2006.01)

(52) U.S. Cl.
CPC ............. *G06T 19/00* (2013.01); *A61B 8/0866* (2013.01); *A61B 8/0883* (2013.01); *A61B 8/13* (2013.01); *G06T 2219/008* (2013.01)

(56) References Cited

U.S. PATENT DOCUMENTS

| | | | |
|---|---|---|---|
| 2007/0255139 A1* | 11/2007 | Deschinger et al. | 600/443 |
| 2010/0256492 A1 | 10/2010 | Lee et al. | |
| 2011/0087094 A1 | 4/2011 | Ohuchi et al. | |
| 2011/0181590 A1* | 7/2011 | Brabec | 345/424 |
| 2011/0213249 A1* | 9/2011 | Nakata et al. | 600/443 |
| 2011/0224546 A1* | 9/2011 | Lee et al. | 600/443 |
| 2011/0282207 A1 | 11/2011 | Hashimoto | |
| 2014/0050381 A1* | 2/2014 | Lee et al. | 382/131 |

FOREIGN PATENT DOCUMENTS

| | | |
|---|---|---|
| EP | 02543319 A1 | 1/2013 |
| EP | 02656790 A1 | 10/2013 |
| JP | 2001-079003 A | 3/2001 |
| JP | 2001-145631 A | 5/2001 |
| JP | 2008-173216 A | 7/2008 |
| JP | 2010-148828 A | 7/2010 |
| KR | 2010-0062838 A | 6/2010 |
| WO | 2011117788 A1 | 9/2011 |

OTHER PUBLICATIONS

Korean Notice of Final Rejection issued in corresponding Korean Patent Application No. 10-2012-0090898, mailed on Apr. 1, 2015; 6 pages with English translation.
Partial European Search Report issued in European application No. 13178932.3 dated Mar. 27, 2014.
Extended European Search Report issued in European application No. 13178932.3 dated Jun. 2, 2014.
Republic of Korea Office Action issued on Jul. 1, 2014 in Republic of Korean Patent Application No. 10-2012-0090898.
Korean Notice of Allowance dated Jun. 15, 2015 issued in Korean Patent Application No. 10-2015-0077483, with English translation.

* cited by examiner

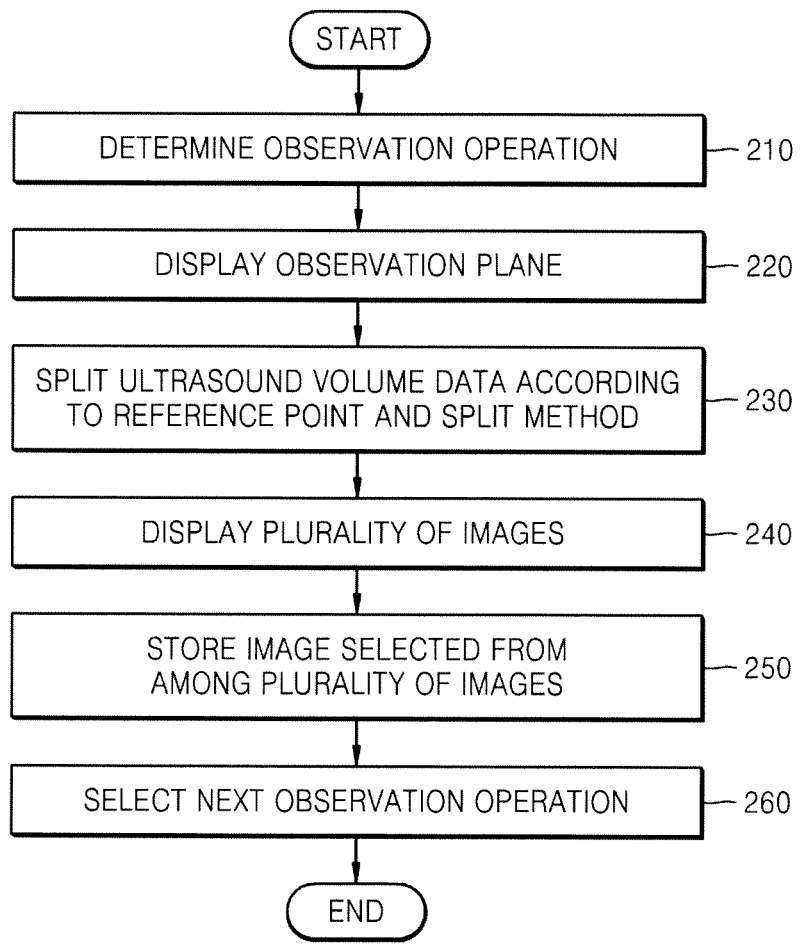

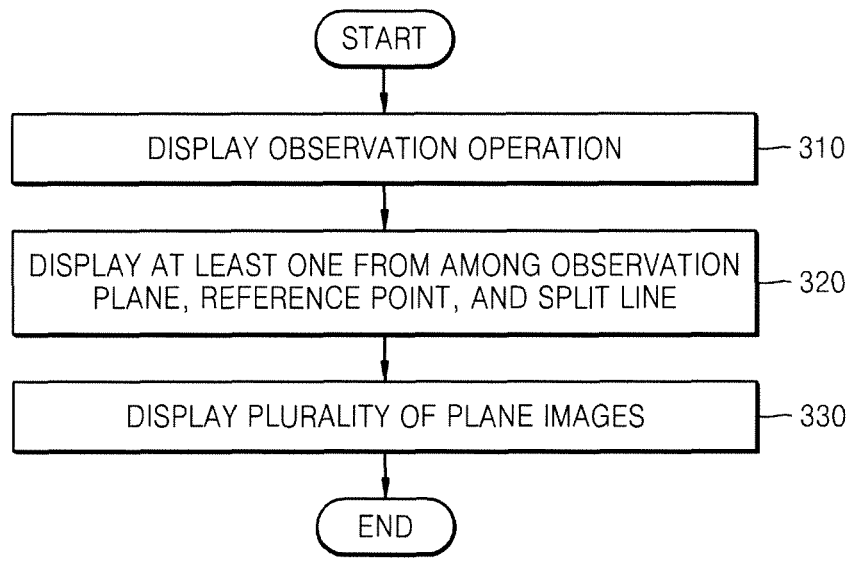

FIG. 5
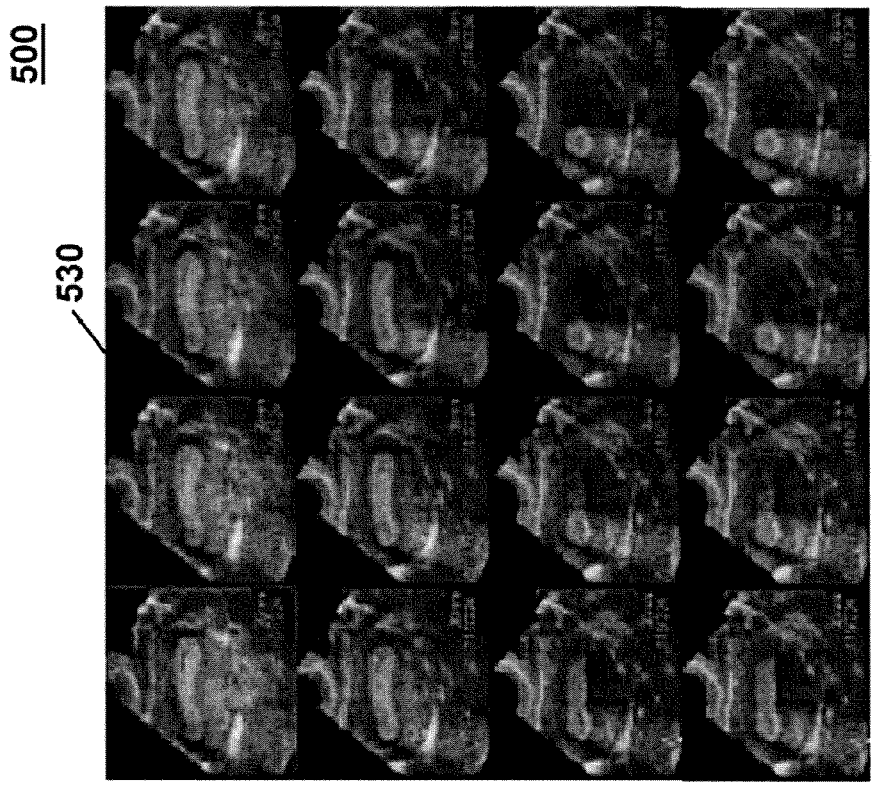
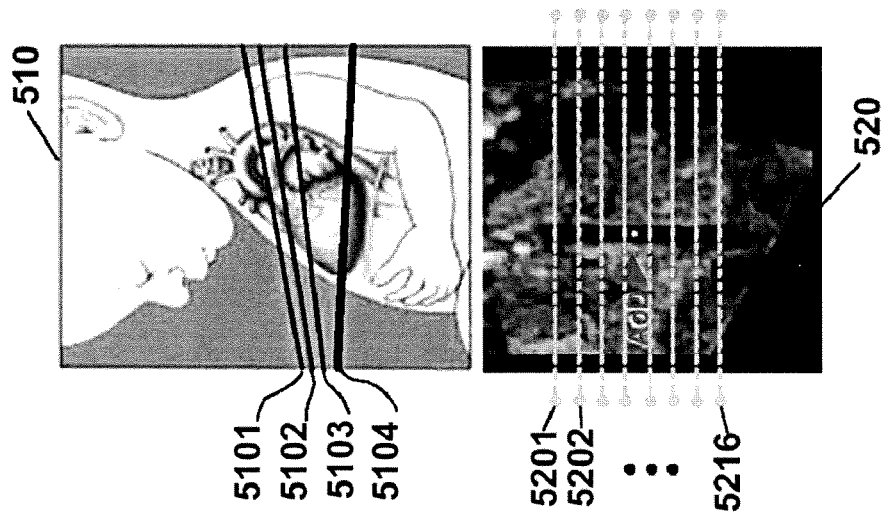

METHOD AND APPARATUS FOR MANAGING AND DISPLAYING ULTRASOUND IMAGE ACCORDING TO AN OBSERVATION OPERATION

CROSS-REFERENCE TO RELATED PATENT APPLICATION

This application claims the benefit of Korean Patent Application No. 10-2012-0090898, filed on Aug. 20, 2012, in the Korean Intellectual Property Office, the disclosure of which is incorporated herein in its entirety by reference.

BACKGROUND OF THE INVENTION

1. Field of the Invention

The present invention relates to a method and apparatus for efficiently managing an ultrasound image of a fetal heart, and a method and apparatus for displaying an ultrasound image for a user to diagnose an object.

2. Description of the Related Art

An ultrasound diagnosis apparatus obtains an image of a desired internal part of an object by generating an ultrasound signal (generally, an ultrasound signal of 20 kHz or higher) by using a probe, and using information about an echo signal reflected from the desired internal part. In particular, the ultrasound diagnosis apparatus is used for medical purposes, e.g., to detect foreign substances in an object, and measure and observe the degree of injury of the object. The ultrasound diagnosis apparatus has been widely used together with other image diagnosis apparatuses, since the ultrasound diagnosis apparatus is more stable, is capable of displaying images in real time, and hardly causes exposure to radiation, compared to an X-ray examination.

Fetal cardiac malformation occupies a large part of fetal diseases. However, a location of a fetal heart frequently varies according to a posture of a fetus within a placenta, unlike an adult's heart. Accordingly, it is very difficult for doctors, who are not sufficiently trained, to obtain an ultrasound image of a fetal heart.

SUMMARY OF THE INVENTION

Many guidelines and protocols have been suggested for users of ultrasound diagnosis apparatuses to efficiently obtain ultrasound images of a fetal heart. However, such guidelines and protocols are inconvenient to use because they include operations, such as rotating, moving, expanding, and scaling down ultrasound volume data along the x-axis, y-axis, and z-axis. Also, much time and effort has to be spent performing measurements for various observation operations of observing a fetal heart.

Thus, the present invention provides a method and apparatus for obtaining and displaying an ultrasound image of a fetal heart from ultrasound volume data. The present invention also provides a computer-readable recording medium having recorded thereon a computer program for performing the method.

According to an aspect of the present invention, there is provided a method of managing an ultrasound image, the method including determining a reference point and an observation plane of ultrasound volume data; obtaining a plurality of images by splitting the ultrasound volume data, based on the reference point and the observation plane; and storing an image selected from among the plurality of images according to an external input signal such that the selected image matches a current observation operation from among a plurality of observation operations for observing an object.

The obtaining of the plurality of images may include obtaining the plurality of images by splitting the ultrasound volume data such that planes that split the ultrasound volume data form a predetermined angle with the observation plane.

The obtaining of the plurality of images may include obtaining the plurality of images by splitting the ultrasound volume data such that planes that split the ultrasound volume data intersect with respect to the reference point.

The obtaining of the plurality of images may include obtaining the plurality of images by adjusting at least one of distances between and a total number of planes that split the ultrasound volume data.

The observation plane may be one of an A-plane, a B-plane, and a C-plane of the object, included in the ultrasound volume data.

The storing of the image selected from among the plurality of images may include storing location information of planes that split the ultrasound volume data, together with the selected image, so as to obtain the selected image.

The method may further include displaying the current observation operation and an image stored to match the current observation operation together.

The displaying of the current observation operation and the image stored to match the current observation operation together may include displaying an exemplary image of the current observation operation.

The method may further include arranging the ultrasound volume data such that a reference region including the reference point is disposed in a determined direction.

The method may further include selecting the current observation operation from among the plurality of observation operations. The selecting of the current observation operation may include selecting the current observation operation from among the plurality of observation operations, according to a predetermined order or an external input signal.

The method may further include selecting one of the plurality of observation operation as a new current observation operation. The method may be repeatedly performed.

According to another aspect of the present invention, there is provided a method of managing an ultrasound image, the method including storing a plurality of pieces of setting information to respectively match a plurality of observation operations for diagnosing an object, each of the plurality of pieces of the setting information including at least one from among information about an observation plane that splits ultrasound volume data in a predetermined direction, information about a split method of splitting the ultrasound volume data, and information about a reference point; displaying a plurality of plane images for a current observation operation which is one of the plurality of observation operations, wherein the plurality of plane images are obtained based on a piece of the setting information matching the current observation operation; and storing an image selected from among the plurality of plane images according to an external input signal such that the selected image matches the current observation operation.

The method may further include repeatedly performing a process of displaying a new observation operation and storing an image to match the new observation operation.

According to another aspect of the present invention, there is provided a method of displaying an ultrasound image, the method including displaying an order of a current observation operation for diagnosing an object in a plurality of observation operation, on a first region of a screen; displaying at least one of an observation plane corresponding to the current observation operation, a reference point, and a split method of splitting ultrasound volume data, on a second region of the screen; and displaying a plurality of images of planes that split the ultrasound volume data based on the observation plane and the reference point, on a third region of the screen.

The current observation operation may be selected from among the plurality of observation operations, according to a predetermined order or an external input signal.

The method may further include marking an image, which is selected from among the plurality of images according to an external input signal, on the third region such that the selected image is differentiated from the other images.

According to another aspect of the present invention, there is provided an ultrasound apparatus including a storage unit for storing ultrasound volume data; an image processing unit for determining a reference point and an observation plane for the ultrasound volume data, and obtaining a plurality of images by splitting the ultrasound volume data, based on the reference point and the observation plane; a display unit for displaying the plurality of images; and a control unit for controlling the storage unit, the image processing unit, and the display unit. The storage unit stores an image selected from among the plurality of images according to an external input signal such that the selected image matches a current observation operation from among a plurality of observation operations for observing an object.

According to another aspect of the present invention, there is provided a computer-readable recording medium having recorded thereon a computer program for executing the method of managing an ultrasound image and the method of displaying an ultrasound image.

BRIEF DESCRIPTION OF THE DRAWINGS

The above and other features and advantages of the present invention will become more apparent by describing in detail exemplary embodiments thereof with reference to the following attached drawings. Here, reference numerals denote structural elements.

FIG. 2 is a flowchart illustrating a method of managing an ultrasound image according to an embodiment of the present invention;

FIG. 3 is a flowchart illustrating a method of displaying an ultrasound image according to an embodiment of the present invention;

FIG. 5 illustrates a process of obtaining a plurality of images and storing an image selected from among the plurality of images, performed by an ultrasound apparatus, according to an embodiment of the present invention;

DETAILED DESCRIPTION OF THE INVENTION

Most of the terms used herein are general terms that have been widely used in the technical art to which the present invention pertains. However, some of the terms used herein may be created to reflect the intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present invention.

In the present specification, it should be understood that the terms, such as 'include' or 'have,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the term ' . . . unit' used herein should be understood as an unit that is capable of performing at least one function or operation and that may be embodied in a hardware or software manner or a combination of hardware and software manners.

As used herein, the term "at least one of," when preceding a list of elements, modify the entire list of elements and do not modify the individual elements of the list.

Hereinafter, exemplary embodiments of the present invention will be described in greater detail.

Figure 1:
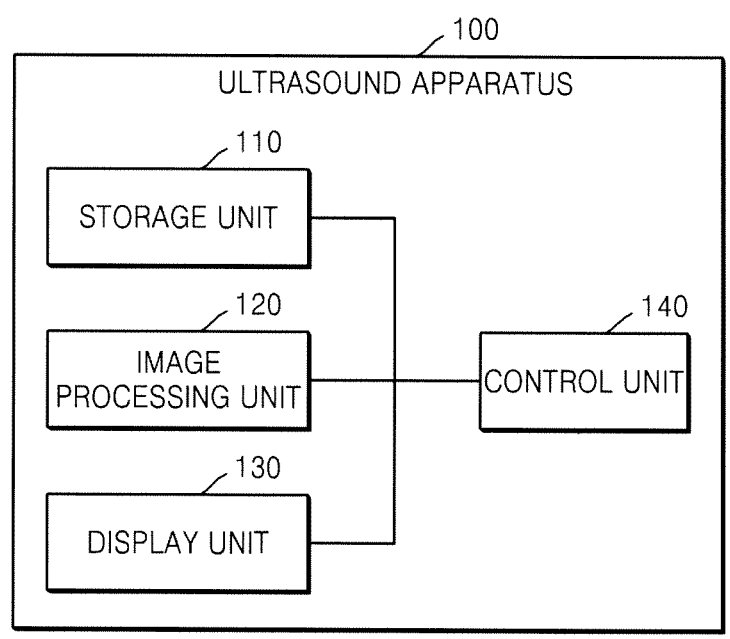
FIG. 1 is a block diagram of an ultrasound apparatus according to an embodiment of the present invention.

FIG. 1 is a block diagram of an ultrasound apparatus 100 according to an embodiment of the present invention. According to an embodiment of the present invention, the ultrasound apparatus 100 may include a storage unit 110, an image processing unit 120, a display unit 130, and a control unit 140. A method of managing and displaying an ultrasound image by using elements of the ultrasound apparatus 100 will now be described in detail.

The storage unit 110 stores ultrasound volume data. The ultrasound volume data stored in the storage unit 110 is obtained by scanning an object with an ultrasound probe. The ultrasound volume data is a three-dimensional (3D) image having a fan shape rather than a rectangular parallelepiped, according to the characteristics of the ultrasound apparatus 100. The present invention will now be described with respect to ultrasound volume data obtained by scanning a fetal heart, but the ultrasound volume data is not limited to data obtained by scanning a human body.

Alternatively, the ultrasound volume data stored in the storage unit 110 may be obtained from a storage medium installed outside the ultrasound apparatus 100. Otherwise, the storage unit 110 may obtain and store the ultrasound volume data by using a picture archiving and communication system (PACS).

The storage unit 110 may further store an ultrasound image. The ultrasound image stored in the storage unit 110 may be a two-dimensional (2D) image or a 3D image. If the ultrasound image is a 2D image, then the 2D image may be an image of a plane obtained by splitting the ultrasound volume data. The ultrasound image stored in the storage unit 110 may be obtained by scanning an object with the ultrasound apparatus 100 or may be received through a PACS, in a wired/wireless manner.

The storage unit 110 may store a plurality of images obtained by the image processing unit 120, and an image selected from among the plurality of images according to an external input signal. Also, the storage unit 110 may store the selected image to match a corresponding observation operation. That is, the storage unit 110 may store images selected to correspond to observation operations such that the selected images may match the observation operations, respectively.

Hereinafter, the term 'observation operation' means a process of observing an object by using an observation plane. In other words, a user may diagnose the object by using an observation plane that has been predetermined for each of the observation operations. More specifically, the ultrasound apparatus 100 may obtain an image by splitting ultrasound volume data based on the observation plane for each of the observation operations, and provide the image to a user. This process will be described in detail with reference to FIGS. 5 to 8 below.

The term 'observation plane' means a plane obtained by splitting volume data in a predetermined direction so as to observe an object. That is, the observation plane is a plane, the location of which varies in the volume data, according to the type of the object to be observed and an observation operation.

Thus, the storage unit 110 may store information regarding observation operations of observing an object and observation planes such that each of the observation operations may match a corresponding observation plane among the observation planes. For each of the observing operations, the storage unit 110 may store information regarding an observation plane and a method of splitting volume data. Also, the storage unit 110 may store information regarding an observation plane matching each of the observation operations, a reference point, and a split method, as setting information.

A 4-chamber view for observing a fetal heart will now be described as an example of an observation operation. The storage unit 110 may store a C-plane as an observation plane for a 4-chamber view observation operation. Also, the storage unit 110 may store information regarding a method of splitting an image of a heart, which is to be observed, by a horizontal straight line, as a split method of splitting volume data on the C-plane. Furthermore, the storage unit 110 may store a center of a descending aorta, as a reference point for rotating the volume data.

According to another embodiment of the present invention, the storage unit 110 may store location information of a plurality of planes obtained by splitting volume data, in the volume data. A method of storing various information to match an observation operation in the storage unit 110, according to an embodiment of the present invention, will be described in detail with reference to FIGS. 5 to 8 below.

The image processing unit 120 determines reference points, observation planes, and split methods with respect to the ultrasound volume data. Information regarding the reference points, observation planes, and split methods may match the respective observation operations. As described above, the information regarding the determined reference points, observation planes, and split methods may be stored in the storage unit 110.

According to one embodiment of the present invention, the information regarding the reference points, observation planes, and split methods that match each of the observation operations may be determined based information input from a user. That is, various information regarding each observation operation may be determined by the image processing unit 120, based on the ultrasound volume data and a predetermined algorithm, or may be determined according to an external input signal. This will be described in detail with reference to FIGS. 4A and 4B below.

Also, the image processing unit 120 obtains a plurality of images by splitting the ultrasound volume data according to a split method, based on a reference point and an observation plane. Any of various split methods may be employed by the image processing unit 120 to split the ultrasound volume data so as to obtain the plurality of images, as will be described in detail with reference to FIGS. 5 and 6 below. Also, the image processing unit 120 may obtain the plurality of images by adjusting distances between and a total number of sub data to be split from the ultrasound volume data.

The display unit 130 may display a plurality of images of planes obtained by splitting the ultrasound volume data, on a screen of the ultrasound apparatus 100. Also, the display unit 130 may display an image stored to match an observation operation from among the plurality of images, together with the observation operation. In addition, the display unit 130 may display an exemplary image of the observation operation.

According to another embodiment of the present invention, the display unit 130 may display an observation operation for an object, which is to be observed, using ultrasound volume data, on a first region of the screen of the ultrasound apparatus 100. Also, the display unit 130 may display at least one from among a reference point, an observation plane matching the observation operation, and a split method of splitting the ultrasound volume data, on a second region of the screen. Furthermore, the display unit 130 may display a plurality of images obtained by splitting the ultrasound volume data, based on the observation plane and the reference point, on a third region of the screen. The current embodiment will be described in greater detail with reference to FIGS. 5 to 7 below.

Also, the display unit 130 may display an order of a current observation operation in all of the observation operations. For example, when an object is diagnosed using a total of five observation operations, that a current observation operation is a second observation operation among the five observation operations may be displayed. Thus, a user may easily understand a whole process, and may select a previous observation operation again through an additional user input.

According to one embodiment of the present invention, the display unit 130 may include a plurality of modules for performing the above operations. For example, the display unit 130 may include an observation operation display module for displaying an order of a current observation operation in all of a plurality of observation operations. Also, the display unit 130 may include a split information display module for displaying at least one from among an observation plane corresponding to the current observation operation, a reference point, and a split method of splitting volume data. Furthermore, the display unit 130 may include a split screen display module for displaying a plurality of images of planes obtained by splitting the volume data.

The display unit 130 may include at least one from among a liquid crystal display (LCD), a thin film transistor-LCD, an organic light-emitting diode (OLED) display, a flexible display, and a 3D display. Alternatively, the ultrasound apparatus 100 may include at least two display units 130 according to a structure thereof.

The control unit 140 controls overall operations of the ultrasound apparatus 100. Also, the control unit 140 may control the storage unit 110, the image processing unit 120, and the display unit 130 to manage and output obtained ultrasound images.

For example, the control unit 140 may control the storage unit 110 to store an image selected for an observation operation such that the selected image may match the observation operation, and may then proceed to a subsequent observation operation. In other words, the control unit 140 may control performing of a plurality of observation operations.

The ultrasound apparatus 100 may further include a user input unit (not shown). The user input unit receives an external input signal for controlling the ultrasound apparatus 100 from a user. For example, the user input unit may receive an external input signal for selecting an image corresponding to a current observation operation from among a plurality of images. Also, the user input unit may receive an external input signal for selecting one of a plurality of observation operations.

The user input unit may receive an external input signal via an input unit, e.g., a keyboard, a mouse, or a stylus pen. Also, the user input unit may receive an external input signal that is input by directly touching or dragging on a liquid crystal screen.

If the display unit 130 and a touch pad (not shown) form a layered structure to manufacture a touch screen, the display unit 130 may act as the user input unit. In this case, the display unit 130 may sense a touched location, area, and pressure of a touch input. The touch screen may sense not only a real touch but also a proximity touch.

A method of managing and displaying an ultrasound image by using the elements of the ultrasound apparatus 100 will now be described with reference to FIGS. 2 and 3. Each of the flowcharts illustrated in FIGS. 2 and 3 includes operations that are sequentially performed by the storage unit 110, the image processing unit 120, the display unit 130, and the control unit 140 of the ultrasound apparatus 100.

FIG. 2 is a flowchart illustrating a method of managing an ultrasound image, according to an embodiment of the present invention. In operation S210, the ultrasound apparatus 100 determines an observation operation. Specifically, the ultrasound apparatus 100 determines an observation operation from among a plurality of observation operations, based on a pre-input order or a user input.

More specifically, for example, when a user desires to observe all of a left atrium, a left ventricle, a right atrium, and a right ventricle of a fetal heart, a 4-chamber view may be appropriate as an observation operation. Also, a 5-chamber view, a 3-vessel & trachea view, a left/right ventricular outflow tract (LVOT/RVOT) view, or an aortic arch view may be used as an observation operation for observing the fetal heart. In addition, it would be apparent to those of ordinary skill in the art that any of various other observation operations may be used.

In operation S220, the ultrasound apparatus 100 displays an observation plane matching the observation operation. Specifically, the ultrasound apparatus 100 may display an observation plane stored to match the observation operation determined in operation S210.

According to an embodiment of the present invention, the observation plane may be an A-plane, a B-plane, or a C-plane. The A-plane may be an observation plane of ultrasound volume data viewed from above. The B-plane may be an observation plane of the ultrasound volume data viewed from a left or right side. The C-plane may be an observation plane of the ultrasound volume data viewed from a front side. That is, the A-plane, the B-plane, and the C-plane mean a transverse plane, a sagittal plane, and a coronal plane of the ultrasound volume data, respectively. Thus, the observation plane may be one of the A-plane, the B-plane, and the C-plane of an object, included in the ultrasound volume data.

According to another embodiment of the present invention, in operation S220, the ultrasound apparatus 100 may display more than one observation plane. That is, the ultrasound apparatus 100 may display all of the observation planes, namely, the A-plane, the B-plane, and the C-plane.

According to another embodiment of the present invention, in operation S220, the ultrasound apparatus 100 may rotate the ultrasound volume data to obtain the observation plane. That is, the ultrasound apparatus 100 may obtain the observation plane matching the observation operation by rotating the ultrasound volume data with respect to a reference point. Information regarding the reference point and the degree of rotating the ultrasound volume data may have been stored to match the observation operation.

In operation S230, the ultrasound apparatus 100 splits the ultrasound volume data according to the reference point and a split method matching the observation operation. The reference point is a point representing a spatial location in the ultrasound volume data, and may be expressed with 3D coordinates. The reference point may also be a location on the observation plane. A process of determining the reference point will be described in detail with reference to FIG. 4 below.

Any of various split methods may be used to split the ultrasound volume data, in operation S230. For example, the ultrasound apparatus 100 may split the ultrasound volume data, such that planes of the ultrasound volume data may intersect with one another or may be disposed apart from one another by a predetermined distance, with respect to the reference point.

For example, a case where the observation plane is the C-plane, i.e., a direction towards a front side of the ultrasound volume data, may be considered. The ultrasound apparatus 100 may determine a plurality of split lines that split the ultrasound volume data in left and right directions of the C-plane. The plurality of split lines may be arranged such that the distances between the plurality of split lines may be the same in a vertical direction with respect to the reference point. The plurality of split lines are shown as one-directional (1D) lines on the observation plane, but may mean planes that split the ultrasound volume data. The ultrasound apparatus 100 may split the ultrasound volume data with the plurality of split lines determined as described above.

The ultrasound apparatus 100 may obtain a plurality of images from a result of splitting the ultrasound volume data in operation S230.

In operation S240, the ultrasound apparatus 100 displays the plurality of images obtained by splitting the ultrasound volume data. That is, the ultrasound apparatus 100 may display the plurality of images as candidates of the observation operation determined in operation S210.

In operation S250, the ultrasound apparatus 100 stores an image selected from among the plurality of images such that the selected image may match the observation operation. The stored image may be selected according to an external input signal, or an image closest to an exemplary image stored in the ultrasound apparatus 100 may be selected by comparing the plurality of images with the exemplary image.

For example, if the observation operation is a 4-chamber view, a user may select one image that most exactly represents the 4-chamber view from among the plurality of images. The ultrasound apparatus 100 may store the selected image to match the 4-chamber view. Thus, when the user selects the 4-chamber view, the user may diagnose the object, based on the selected image stored to match the 4-chamber view. The user may conveniently and efficiently diagnose the object, based on images stored to match the 4-chamber view and other various observation operations.

In operation S260, the ultrasound apparatus 100 selects a next observation operation. As described above, the next observation operation may be selected according to an order that has been previously input to the ultrasound apparatus 100, or may be selected according to an external input signal.

For example, the ultrasound apparatus 100 may store an image matching the observation operation which is the 4-chamber view, and then select the 5-chamber view as the next observation operation according to the previously input order. The image processing unit 120 may determine the 4-chamber view, the 5-chamber view, the 3-vessel & trachea view, or the like, as an observation operation, based on an external input signal received via the user input unit.

FIG. 3 is a flowchart illustrating a method of displaying an ultrasound image, according to an embodiment of the present invention. In operation S310, the display unit 130 may display an observation operation of ultrasound volume data for an object that is to be observed, on the first region of the screen of the ultrasound apparatus 100. In other words, the display unit 130 may display the observation operation that is manually or automatically determined by the image processing unit 120 according to an external input signal.

The displaying of the observation operation means displaying a location of a viewpoint for observing the object in the ultrasound volume data. For example, the display unit 130 may display an image of the object, e.g., a fetal heart, and a position of the 4-chamber view which is the observation operation, as will be described in detail with reference to FIGS. 5 and 6.

In operation S320, the display unit 130 may display at least one from among an observation plane matching the observation operation, a reference point, and a split line for splitting the ultrasound volume data, on the second region of the screen of the ultrasound apparatus 100. As described above, the split line for splitting the ultrasound volume data may be determined according to a split method stored to match the observation operation.

If the observation operation is the 4-chamber view, the display unit 130 may display a C-plane as the observation plane, and display a plurality of split lines that split the ultrasound volume data on the observation plane. Also, the display unit 130 may display a split method of splitting the ultrasound volume data in a left direction and a right direction of the observation plane, with respect to the reference point.

In operation S330, the display unit 130 may display a plurality of images of planes obtained by splitting the ultrasound volume data based on the split method and the reference point, on the third region of the screen of the ultrasound apparatus 100. The plurality of images may be images obtained by splitting the ultrasound volume data by the image processing unit 120. Alternatively, each of the images may be obtained by splitting the ultrasound volume data by using one of the plurality of split lines displayed on the second region.

A user may efficiently diagnose the object, based on content displayed on the first to third regions of the screen of the ultrasound apparatus 100 by the display unit 130. That is, an ultrasound image for diagnosing the object may be conveniently obtained based on the observation operation, the observation plane, and the plurality of images of planes obtained by splitting the ultrasound volume data.

Figure 4A:
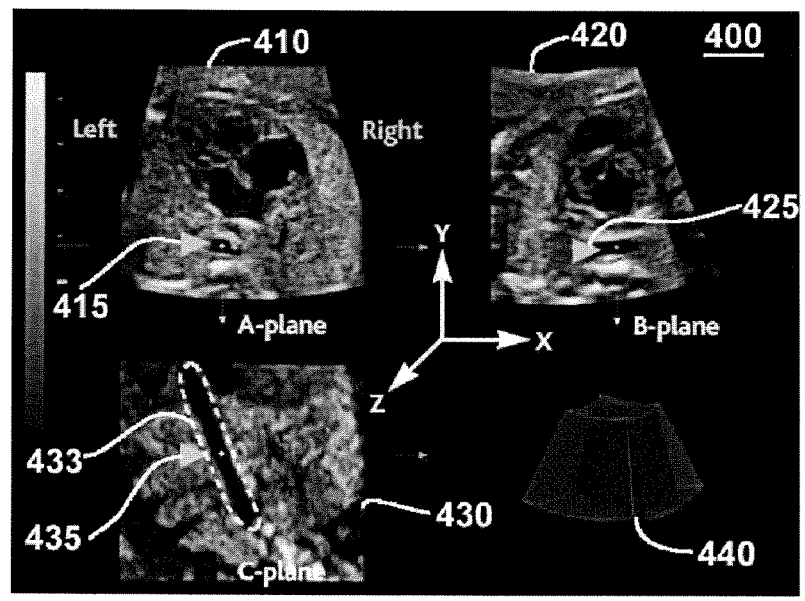
FIGS. 4A and 4B are images illustrating a process of determining a reference point, performed by an ultrasound apparatus, according to an embodiment of the present invention.
Figure 4B:
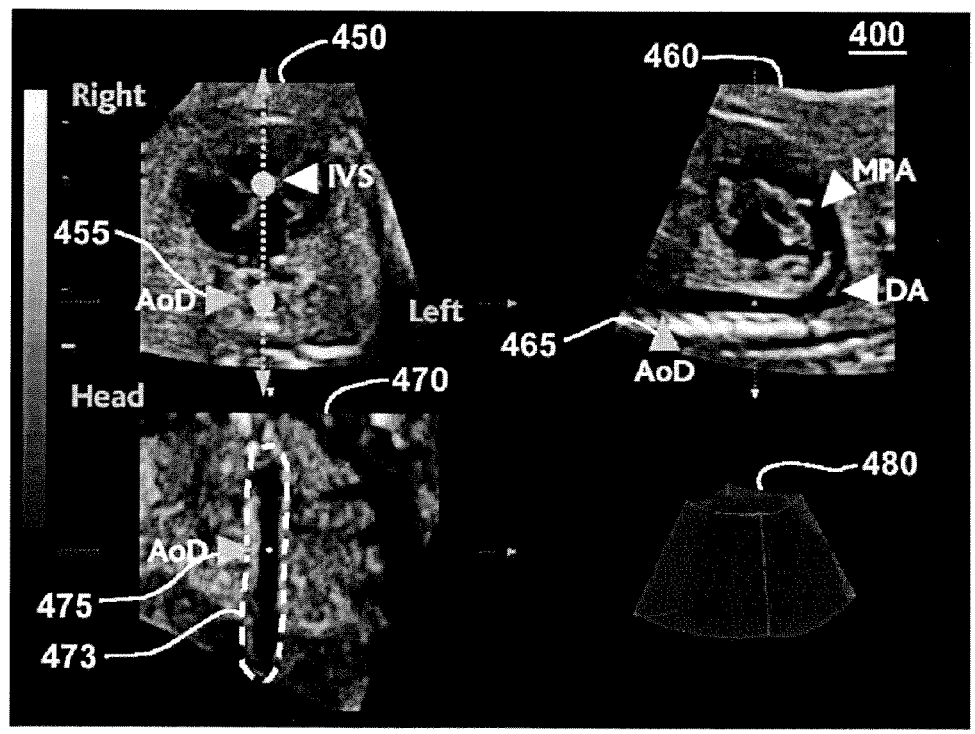

FIGS. 4A and 4B are images illustrating a process of determining a reference point, performed by the ultrasound apparatus 100, according to an embodiment of the present invention.

Referring to FIG. 4A, the display unit 130 of the ultrasound apparatus 100 may display an image 410 of an A-plane of ultrasound volume data 440, an image 420 of a B-plane of the ultrasound volume data 440, an image 430 of a C-plane of ultrasound volume data 440, and the ultrasound volume data 440 on a left upper portion, a right upper portion, a left lower portion, and a right lower portion of a screen 400 of the ultrasound apparatus 100, respectively. The display unit 130 may output the image 410 of the A-plane, the image 420 of the B-plane, and the image 430 of the C-plane of the ultrasound volume data 440 stored in the storage unit 110, to the screen 400 of the ultrasound apparatus 100.

Referring to FIG. 4A, the image processing unit 120 may determine reference points 415, 425, and 435 of the ultrasound volume data 440. According to an embodiment of the present invention, the image processing unit 120 may determine the reference points 415, 425, and 435 from a 4-chamber view or may determine centers of images of a descending aorta AoD shown in the 4-chamber view, as the reference points 415, 425, and 435. In this case, when the image processing unit 120 identifies the descending aorta AoD from the 4-chamber view, the centers of images of the descending aorta AoD may be automatically determined as the reference points 415, 425, and 435. Alternatively, the user input unit of the ultrasound apparatus 100 may receive an external input signal for selecting a center of the descending aorta AoD, and the image processing unit 120 may determine the reference points 415, 425, and 435, based on the external input signal.

Although FIG. 4A illustrates a process of determining the reference points 415, 425, and 435 through the 4-chamber view of the ultrasound volume data 440, the image processing unit 120 may determine the reference points 415, 425, and 435 through various observation operations other than the 4-chamber view.

The storage unit 110 stores the determined reference points 415, 425, and 435. According to an embodiment of the present invention, the storage unit 110 may store the reference points 415, 425, and 435 to match respective observation operations as described above.

In FIG. 4A, a reference region 433, including the reference point 435, is shown in the image 430 of the C-plane. A process of arranging an image 450 of an A-plane, an image 460 of a B-plane, an image 470 of a C-plane, and ultrasound volume data 480 with respect to a reference region 473 will now be described with reference to FIG. 4B.

Referring to FIG. 4B, a central point 475 and the reference region 473 are shown in the image 470 of the C-plane. FIG. 4B illustrates the image 450 of the A-plane, the image 460 of the B-plane, and the image 470 of the C-plane obtained by rotating the image 410 of the A-plane, the image 420 of the B-plane, and the image 430 of the C-plane with respect to the reference point 435 (or, central point 475) by the image processing unit 120 in such a manner that the reference region 433 of FIG. 4A may be vertically disposed.

Not only a reference point but also other criteria for ultrasound volume data are needed for the ultrasound apparatus 100 to obtain a plurality of images split from the ultrasound volume data according to an observation plane. This is because the ultrasound volume data is a 3D image. That is, a location of the 3D image cannot be exactly expressed only with one point. Thus, not only the reference point 435 but also other criteria should be determined to split the ultrasound volume data according to the observation plane.

In the current embodiment, the image processing unit 120 determines the other criteria for the 4-chamber view of the ultrasound volume data 440 by rotating the reference region 433, including the reference point 435, to be vertically disposed. However, the present invention is not limited thereto, and any of other various methods may be used to determine the other criteria for the ultrasound volume data 440. Any of other various methods may be performed with respect to observation operations other than the 4-chamber view.

A process of arranging the ultrasound volume data 440 and the image 410 of the A-plane, the image 420 of the B-plane, and the image 430 of the C-plane, performed by the image processing unit 120, will now be described in more detail. According to an embodiment of the present invention, the image processing unit 120 may reverse a brightness value of the image 430 of the C-plane of the 4-chamber view, based on a predetermined brightness value. Then, the image processing unit 120 may determine an object to be rotated, based on an 8- or 4-connected component analysis algorithm and a skeletonization algorithm. Furthermore, the ultrasound volume data 440 may be rotated by checking an inclination angle of a determined reference region.

In a method of rotating the ultrasound volume data 440, the image 410 of the A-plane, the image 420 of the B-plane, and the image 430 of the C-plane according to another embodiment of the present invention, the brightness value of the image 430 of the C-plane may be reversed and two boundary lines may be detected according to an edge detection algorithm. Then, the boundary lines may be arranged to be vertically disposed. Alternatively, any of other various methods may be used to arrange the image 410 of the A-plane, the image 420 of the B-plane, and the image 430 of the C-plane of the ultrasound volume data 440.

The image processing unit 120 may determine criteria for splitting the ultrasound volume data 480 to obtain a plurality of images by obtaining the reference region 473. That is, if an image of the descending aorta AoD illustrated as a reference region is vertically disposed on a C-plane, then the image processing unit 120 may obtain images for various observation operations by splitting resultant ultrasound volume data.

FIG. 5 illustrates a process of obtaining a plurality of images and storing an image selected from among the plurality of images, performed by the ultrasound apparatus 100, according to an embodiment of the present invention. A case where the image processing unit 120 determines a 4-chamber view as an observation operation will now be described.

The display unit 130 may display the 4-chamber view as an observation operation on a first region 510 of a screen 500 of the ultrasound apparatus 100. That is, the display unit 130 may display a location of a plane corresponding to a 4-chamber view for observing a fetal heart, in the volume data.

Hereinafter, the terms 'first region', 'second region', and 'third region' denote a plurality of regions displayed on a screen of the ultrasound apparatus 100, regardless of the order thereof. In other words, each of these terms may be selected for convenience of explanation, regardless of locations thereof on the screen of the ultrasound apparatus 100.

In FIG. 5, four observation operations 5101, 5102, 5103, and 5104 are displayed on the first region 510, and a current observation operation 5104 which is a 4-chamber view is thickly displayed from among these observation operations. Here, the term 'current observation operation' may mean an observation plane on which a process of selecting and storing an image is performed based on previously stored information about an observation plane, a reference point, and a split method, from among these observation operations.

The display unit 130 may display an observation plane corresponding to the current observation operation 5104 and a plurality of split lines 5201, 5202, . . . , 5216 for splitting ultrasound volume data, on a second region 520 of the screen 500. The display unit 130 may further display a reference point matching the current observation operation 5104.

As described above, when the 4-chamber view is determined as an observation operation, the 4-chamber view corresponds to an image of an A-plane obtained by horizontally splitting the ultrasound volume data. That is, a plane obtained by horizontally splitting the ultrasound volume data based on the image of the C-plane is the 4-chamber view. Thus, the display unit 130 may display the C-plane as the observation plane and the plurality of split lines 5201, 5202, . . . , 5216 that horizontally split the image of the C-plane.

On the other hand, since the image of the A-plane may also be obtained by horizontally splitting an image of a B-plane, the image processing unit 120 may determine a reference point based on the B-plane. In this case, the display unit 130 may display a plurality of split lines that horizontally split the image of the B-plane.

Then, the image processing unit 120 may obtain a plurality of images by splitting the ultrasound volume data. That is, the image processing unit 120 may obtain images of planes obtained by splitting the ultrasound volume data by using the plurality of split lines 5201, 5202, . . . , 5216. The images of the planes may be 2D images of planes obtained by splitting the ultrasound volume data with respect to a reference point determined for the current observation operation 5104.

According to an embodiment of the present invention, the image processing unit 120 may obtain a plurality of images by adjusting the distances between or a total number of the plurality of split lines 5201, 5202, . . . , 5216 that split the ultrasound volume data. That is, the image processing unit 120 may obtain a plurality of images by more densely or sparsely splitting the ultrasound volume data by arbitrarily adjusting the distances between the plurality of split lines 5201, 5202, . . . , 5216. Otherwise, the image processing unit 120 may adjust the number of images to be obtained by adjusting the total number of split lines 5201, 5202, . . . , 5216.

Then, the display unit 130 may display the images of the planes obtained by splitting the ultrasound volume data by using the plurality of split lines 5201, 5202, . . . , 5216, on a third region 530 of the screen 530. For example, sixteen images displayed on the screen 500 of the ultrasound apparatus 100 are images of planes obtained by splitting the ultrasound volume data by using the plurality of split lines 5201, 5202, . . . , 5216 displayed on the second region 520.

Then, the user input unit may receive an input for selecting one of the plurality of images from a user. That is, the display unit 130 may receive an input for selecting an image that most exactly represents the 4-chamber view from among the images of the planes obtained by splitting the ultrasound volume data, from the user. Further, the storage unit 110 may store an image selected according to an external input signal to match an observation operation.

According to an embodiment of the present invention, when the selected image is stored to match the observation operation, the storage unit 110 may also store either information about split lines that split the ultrasound volume data or location information of a plane corresponding to the selected image so as to obtain the selected image. For example, a case where the image selected from among the plurality of images displayed in FIG. 5 corresponds to the plane obtained by splitting the ultrasound volume data by using the last split line 5216 from among the plurality of split lines 5201, 5202, . . . , 5216 displayed on the second region 520 may be considered. In this case, the storage unit 110 may store information about the 4-chamber view which is the observation operation, the selected image, and the last split line 5216. Otherwise, the storage unit 110 may store the location information of the plane based on the last split line 5216, instead of the last split line 5216.

According to another embodiment of the present invention, the storage unit 110 may store not only an image selected from among a plurality of images, which are obtained by the image processing unit 120, according to an external input signal, but also the other images. Thus, if the current observation operation 5104 is selected again, the display unit 130 may display the stored plurality of images again and the image processing unit 120 thus needs not to split the ultrasound volume data again. According to this embodiment, a time needed for the image processing unit 120 to split the ultrasound volume data may be reduced.

FIG. 5 illustrates a result of splitting ultrasound volume data based on the C-plane as an observation plane and the plurality of split lines 5201, 5202, . . . , 5216 which are parallel lines, performed by the image processing unit 120. In other words, the plurality of split lines 5201, 5202, . . . , 5216 are displayed as parallel lines on the C-plane which is an observation plane, but actually correspond to planes that split the ultrasound volume data.

However, although the planes that split the ultrasound volume data are displayed in parallel on the C-plane which is an observation plane, the planes may not be parallel with one another, as shown on the first region 510. That is, each of the planes that split the ultrasound volume data may form a predetermined angle with respect to the C-plane which is an observation plane.

In other words, the planes that split the ultrasound volume data may split the ultrasound volume data to be parallel with the A-plane which is an observation plane, but may split the ultrasound volume data not to be parallel with the A-plane, as shown in the first region 510. In other words, the image processing unit 120 may split the ultrasound volume data such that the planes that split the ultrasound volume data may contact the A-plane.

The ultrasound volume data may be split according to any of various methods other than the method described with reference to FIG. 5. A method of splitting the ultrasound volume data, according to another embodiment of the present invention, will be described with reference to FIG. 6 below.

Figure 6:
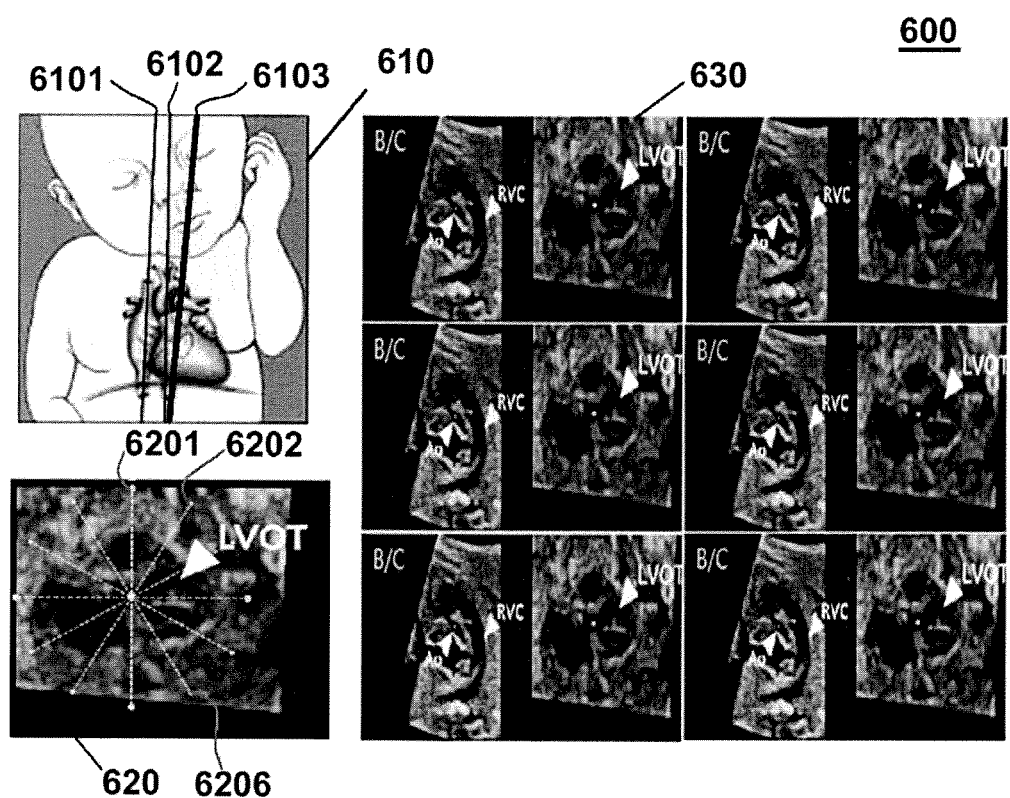
FIG. 6 illustrates a process of obtaining a plurality of images and storing an image selected from among the plurality of images, performed by an ultrasound apparatus, according to another embodiment of the present invention.

FIG. 6 illustrates a process of obtaining a plurality of images and storing an image selected from among the plurality of images, performed by an ultrasound apparatus, according to another embodiment of the present invention.

Similar to the process of FIG. 5, the display unit 130 may display an observation operation on a first region 610 of a screen 600 of the ultrasound apparatus 100. Similarly, the display unit 130 may display a plurality of split lines 6201, 6202, . . . , 6206 that split ultrasound volume data based on the observation plane, on a second region 620 of the screen 600, and may display a plurality of images obtained by splitting the ultrasound volume data by using the plurality of split lines 6201, 6202, . . . , 6206, on a third region 630 of the screen 600.

FIG. 6 illustrates a case where an LVOT view is determined as the observation operation for the ultrasound volume data. The LVOT view is an observation operation for observing a left ventricular outflow tract and corresponds to an image of a B-plane. The display unit 130 may display the determined observation operation on the first region 610 of the screen 600. According to an embodiment of the present invention, the display unit 130 may display an observation operation, which is determined by the image processing unit 120, thickly or using a different color, so that a user may easily distinguish the determined observation operation from other observation operations. In FIG. 6, an LVOT view 6103 is displayed thickly.

In the current embodiment, the image processing unit 120 may determine a reference point of the ultrasound volume data from a 5-chamber view image, to correspond to the LVOT view which is the observation operation.

Also, in the current embodiment, the image processing unit 120 may determine an A-plane as an observation plane. That is, since the LVOT view corresponds to a B-plane, an image corresponding to the LVOT view may be selected from among a plurality of images obtained by splitting the ultrasound volume data by using split lines displayed on the A-plane.

Similar to the 4-chamber view, the 5-chamber view corresponds to an A-plane and is an observation operation for observing not only a left atrium, a left ventricle, a right atrium, and a right ventricle of a fetal heart but also an aorta. In the current embodiment, the image processing unit 120 may determine a center of an aorta observed from the 5-chamber view, as a reference point.

Then, the image processing unit 120 may obtain a plurality of images split from the ultrasound volume data, based on the observation plane and the reference point. In other words, the image processing unit 120 may obtain a plurality of images split from the ultrasound volume data by using the plurality of split lines 6201, 6202, . . . , 6206 displayed on the second region 620 of the screen 600.

Unlike in the process of FIG. 5, the plurality of images may be obtained by splitting the ultrasound volume data such that planes that split the ultrasound volume data may intersect with respect to the reference point, according to the process of FIG. 6.

That is, the image processing unit 120 may split the ultrasound volume data such that the plurality of split lines 6201, 6202, . . . , 6206 may intersect with reference to the reference point, on the A-plane which is the observation plane. The plurality of split lines 6201, 6202, . . . , 6206 correspond to the planes that split the ultrasound volume data, respectively. Accordingly, the planes that split the ultrasound volume data intersect with reference to the reference point.

As described above, since the ultrasound volume data is split, based on the plurality of split lines 6201, 6202, . . . , 6206 displayed on the A-plane, each of the plurality of images is a B-plane or a C-plane. The display unit 130 may display the images of the planes that split the ultrasound volume data, on the third region 630 of the screen 600.

A process of storing an image selected from among the plurality of images according to an external input signal so as to match the observation operation, performed by the storage unit 110, is as described above with reference to FIG. 5.

Figure 7:
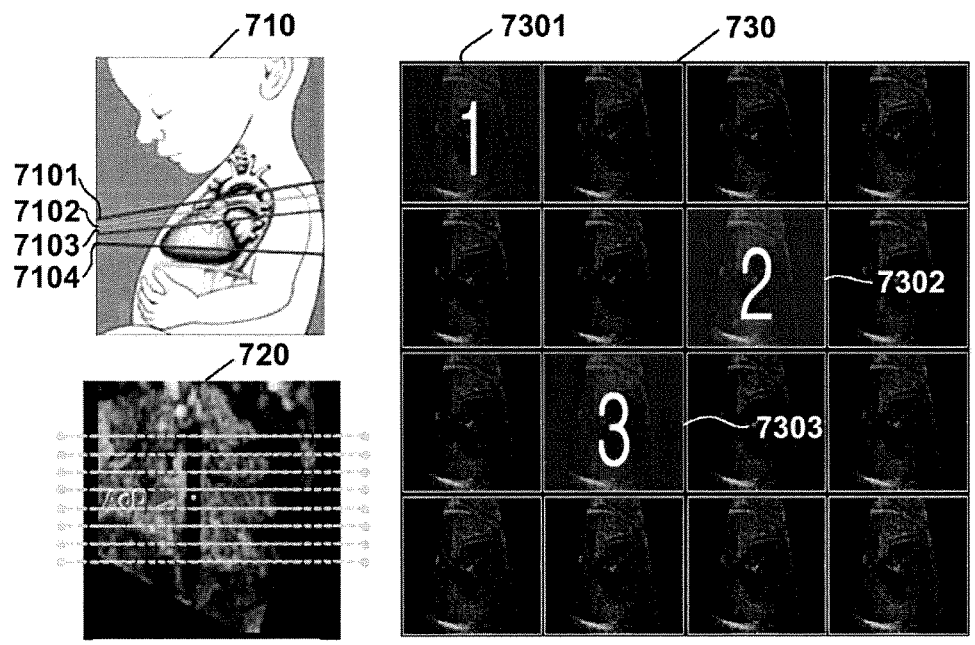
FIG. 7 illustrates a process of storing an image selected from among a plurality of images according to an external input image such that the selected image may match an observation operation, according to an embodiment of the present invention.

FIG. 7 illustrates a process of storing an image selected from among a plurality of images according to an external input signal such that the selected image may match an observation operation, according to an embodiment of the present invention.

As described above with reference to FIGS. 5 and 6, the display unit 130 may display a plurality of images split from ultrasound volume data, and the storage unit 110 may store an image selected from the plurality of images according to an external input signal such that the selected image may match an observation operation. Contents displayed on a first region 710, a second region 720, and a third region 730 of a screen of the ultrasound apparatus 100 by the display unit 130 are substantially the same as those described above with reference to FIGS. 5 and 6.

In the current embodiment, the ultrasound apparatus 100 may repeatedly perform the process described above with reference to FIG. 5 or 6 with respect to a plurality of observation operations. That is, the ultrasound apparatus 100 stores the selected image to match a first observation operation from among the plurality of observation operations.

Then, the ultrasound apparatus 100 selects a second observation operation as a next observation operation, and performs the process, which was performed with respect to the first observation operation, with respect to the second observation operation. However, in this case, a plurality of images are obtained using a reference point, an observation plane, and a split method matching the second observation operation.

After an image selected from among a plurality of images is stored to match the second observation operation, the ultrasound apparatus 100 performs the process with respect to the other operations, e.g., a third observation operation, a fourth observation operation, and so on. As described above, an order of selecting the plurality of observation operations may be determined according to a protocol that has been input to the ultrasound apparatus 100.

For example, after a user selects an image 7301 from among a plurality of images of a 4-chamber view 7104 and the ultrasound apparatus 100 stores the image 7301 to match the 4-chamber view 7104, a 5-chamber view 7103 may be determined as a subsequent observation operation. Then, the storage unit 110 may store an image 7302 selected from among the plurality of images based on an input received from a user, such that the image 7301 may match the 5-chamber view 7103. Similarly, the ultrasound apparatus 100 may display a plurality of images of a main pulmonary artery view 7102, and may store an image 7303 selected from among the plurality of images according to an external input signal such that the image 7303 may match the main pulmonary artery view 7102.

Alternatively, a user himself or herself may select an observation operation f. After an image matching the third observation operation is stored, the ultrasound apparatus 100 may receive an external input signal for selecting the first observation operation when the user desires to replace the image matching the first observation operation with a new image.

For example, a case where the observation operation is a 5-chamber view and the second observation operation is an LVOT view will now be described. As described above with reference to FIG. 5, the image processing unit 120 may use a C-plane as an observation plane to obtain a plurality of images matching the 5-chamber view which is the first observation operation. In other words, the image processing unit 120 may determine a center of a descending aorta shown in an image of the C-plane, as a reference point, and may split ultrasound volume data to obtain a plurality of A-plane images.

After the storage unit 110 stores one of the plurality of A-plane images to match the 5-chamber view, the control unit 140 may control the image processing unit 120 to determine the LVOT view as the second observation operation, according to a predetermined order or an external input signal. When the image processing unit 120 determines the LVOT view as the second observation operation, a C-plane image may be used as an observation plane. Further, the image processing unit 120 may determine a new reference point of the C-plane image. That is, the image processing unit 120 may determine a center of an aorta shown in the C-plane image as a new reference point of the second observation operation.

Examples of an observation operation may include not only the 4-chamber view and the 5-chamber view described above but also other various observation operations. A 3-vessel & trachea view, an LVOT/RVOT view, and an aortic arch view may be used as observation operations as described above. Also, a ductal arch view, a superior vena cava (SVC) view, an inferior vena cava (IVC) view, and upper abdomen with the stomach view, and the like may be used as observation operations.

By repeatedly performing the process described above, the ultrasound apparatus 100 may store images selected by a user such that the selected images may automatically match various observation operations, respectively. Thus, the user may himself or herself efficiently diagnose an object without having to process ultrasound volume data with respect to each of various observation operations.

According to an embodiment of the present invention, when the ultrasound apparatus 100 performs image matching while changing observation operations, if the changed observation operations correspond to the same type of observation plane, then the display unit 130 may display an image without changing observation planes. For example, all of the 4-chamber view, the 5-chamber view, and the 3-vessel & trachea view are observation operations corresponding to an A-plane and may thus match a C-plane as an observation plane. Thus, as a current observation operation is sequentially switched to other observation operations, the ultrasound apparatus 100 may perform image display by simply switching between the split lines 7101, 7102, 7103, and 7104 to be thickly displayed on the first region 710 while maintaining the observation plane 720. According to the current embodiment, the ultrasound apparatus 100 may avoid unnecessary changing of observation planes.

In the previous embodiment, the ultrasound apparatus 100 may determine an order of a plurality of observation operations according to the types of observation planes matching the plurality of observation operations. In other words, when the ultrasound apparatus 100 displays observation operations corresponding to the same observation plane, e.g., an A-plane, a B-plane, or a C-plane, in a consecutive order, a change in content to be displayed may be minimized.

According to another embodiment of the present invention, although not shown in FIG. 7, the display unit 130 may display a name of an observation operation on the screen of the ultrasound apparatus 100. For example, the display unit 130 may not only display images of respective observation operations but also display names of the respective observation operations in the form of text, on the first region 710 of the screen. Thus, a user may view the images of the respective observation operations displayed on the first region 710 and may further exactly identify a current observation operation.

According to another embodiment of the present invention, the display unit 130 may mark the images 7301, 7302, and 7303, which are respectively selected with respect to observation operations according to an external input signal, to be differentiated from other images. Specifically, the display unit 130 may express the images 7301, 7302, and 7303 selected from among images displayed on the third region 730 of the screen with a different chroma or color, mark a number indicating that the selected images 7301, 7302, and 7303 are selected, or mark names of the observation operations matching the respective selected images 7301, 7302, and 7303. Thus, a user may select an image of the current observation operation, based on marked images selected with respect to the observation operations.

Figure 8:
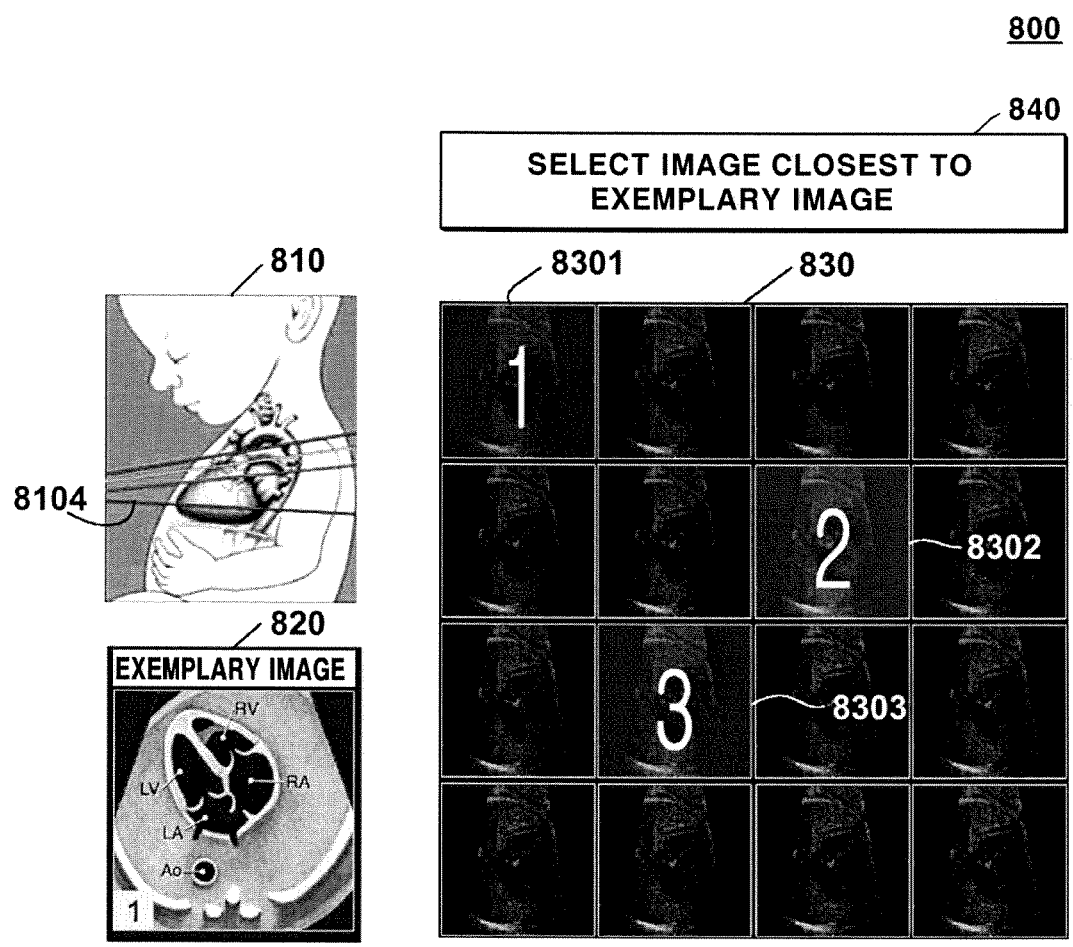
FIG. 8 illustrates a process of displaying an exemplary image of an observation operation, according to an embodiment of the present invention.

FIG. 8 illustrates a process of displaying an exemplary image of an observation operation, according to an embodiment of the present invention.

In FIG. 8, the display unit 130 may display an exemplary image of a determined observation operation 8104 on a second region 820 of a screen 800, instead of a plurality of split lines that split ultrasound volume data. In other words, the display unit 130 may display exemplary images of respective observation operations, stored in the storage unit 110, so that an image may be selected from among a plurality of images, based on an ideal ultrasound image of a selected observation operation. Here, an exemplary image may be a real image obtained from an object but may be a simple picture as illustrated in FIG. 8.

Referring to the embodiment of FIG. 8, the display unit 130 may display an exemplary image of a 4-chamber view on the second region 820, and a user may select an image that most exactly represents the 4-chamber view from among a plurality of images displayed on a third region 830 of the screen 800, based on the exemplary image.

FIG. 8 illustrates that the display unit 130 displays the exemplary image on the second region 820, but split lines that split ultrasound volume data may be displayed on the second region 820 as illustrated in FIGS. 5 to 7 and the exemplary image may be displayed on a fourth region (not shown) of the screen 800. According to another embodiment of the present invention, the display unit 130 may further display a text 840 which a user may refer to, on the screen 800 of the ultrasound apparatus 100.

Before describing FIGS. 9 and 10, an additional embodiment of the present invention will be described with reference to FIG. 11. FIG. 11 illustrates that the display unit 130 displays a screen 1100 including the first to third regions 710 to 730 shown in FIG. 7, together with a flowchart 1110 of an observation operation, according to an embodiment of the present invention. That is, the display unit 130 may display an order of a current observation operation in all of a plurality of observation operations.

For example, as illustrated in FIG. 11, when a 4-chamber view, a 5-chamber view, and a 3-vessel & trachea view are sequentially performed, the display unit 130 may display this order. Although not shown in FIG. 11, if a current observation operation is the 5-chamber view, the display unit 130 may display a region corresponding to the 5-chamber view, with a rectangle or with a different color so that the image region may be visually differentiated from other regions.

In relation to the embodiment of FIG. 11, the ultrasound apparatus 100 may select another observation operation according to an external input signal. If a current observation operation is the 5-chamber view and a user desires to change an image stored to match the 4-chamber view, the ultrasound apparatus 100 may receive an external input signal, e.g., an input of touching a region matching the 4-chamber view. Thus, the ultrasound apparatus 100 may switch the current observation operation from the 5-chamber view to the 4-chamber view, and store a new image of the 4-chamber view by displaying images of planes that split ultrasound volume data again.

According to the embodiment of FIG. 11, a user may easily check an order of the current observation operation in all of the observation operations, and may arbitrarily change the order of the observation operations.

Figure 9:
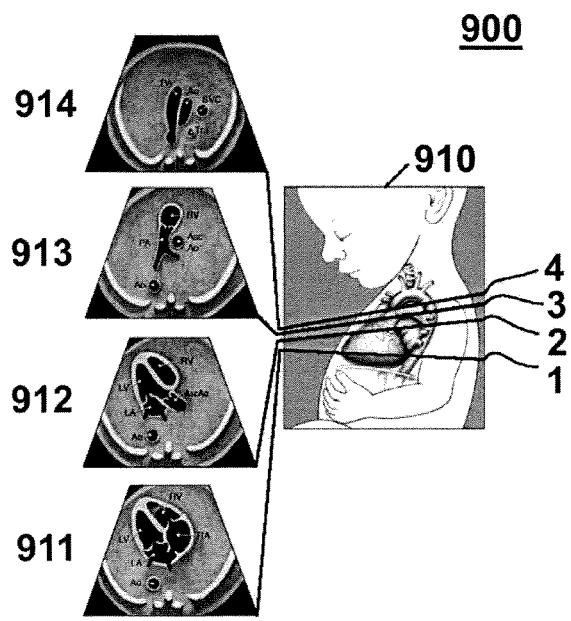
FIG. 9 is a diagram illustrating a process of displaying an observation operation together with an image corresponding to the observation operation, according to an embodiment of the present invention.
Figure 10:
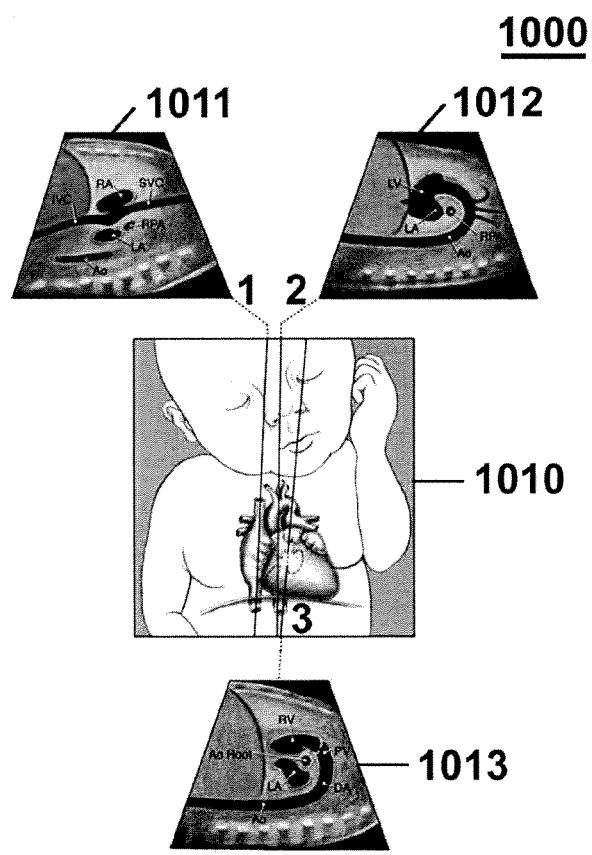
FIG. 10 is a diagram illustrating a process of displaying an observation operation together with an image corresponding to the observation operation, according to another embodiment of the present invention.
Figure 11:
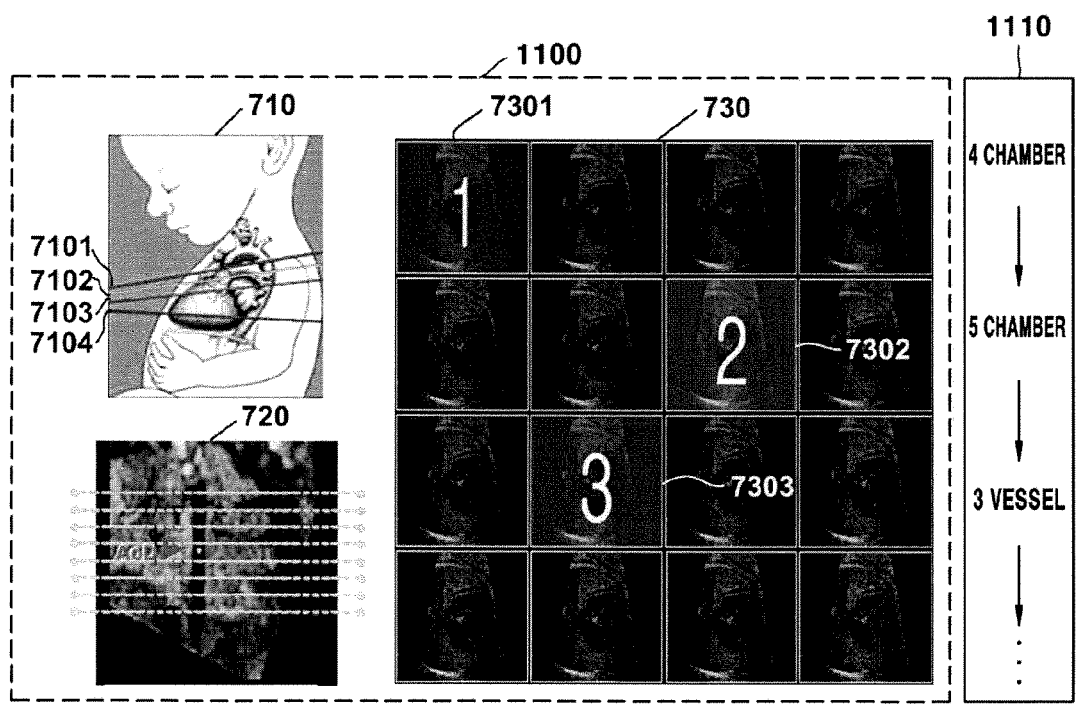
FIG. 11 is a diagram illustrating a process of displaying an order of a current observation operation in all of the observation operations, according to an embodiment of the present invention.

FIGS. 9 and 10 are diagrams illustrating processes of displaying an observation operation together with an image corresponding to the observation operation, according to embodiments of the present invention.

According to an embodiment of the present invention, the display unit 130 may display an image stored to match an observation operation, together with the observation operation. If images that are respectively selected for a plurality of observation operations according to an external input signal are stored, the display unit 130 may display the selected images together with the plurality of observation operations corresponding thereto.

Referring to the embodiment illustrated in FIG. 9, the display unit 130 may display not only four observation operations 1, 2, 3, and 4 on a first region 910 but also images 911, 912, 913, and 914 stored to respectively correspond to the observation operations 1, 2, 3, and 4.

According to an embodiment of the present invention, unlike in FIG. 9, the display unit 130 may expand and display only an image corresponding to an observation operation selected from among the four observation operations 1, 2, 3, and 4.

Specifically, when one of the observation operations 1, 2, 3, and 4 is selected according to a user input received via the user input unit, the display unit 130 may expand and display only image stored to correspond to the selected observation operation, without displaying all of the images 911, 912, 913, and 914. Thus, a user may observe the image matching the selected observation operation in a larger size than when all of the images 911, 912, 913, and 914 are displayed.

According to another embodiment of the present invention, while the display unit 130 displays an observation operation and an image corresponding thereto, the control unit 140 may control the storage unit 110 to store a new image corresponding to the observation operation, based on a received user input. That is, when a user determines that the image stored to correspond to the observation operation is not appropriate and thus desires to store a new image corresponding to the observation operation, the control unit 140 may control the display unit 130 to display a plurality of images, which are obtained for the observation operation by using the image processing unit 120, again.

For example, when a user desires to change an image stored for a 4-chamber view, the user input unit may receive an external input signal that instructs to select a new image from the user. Thus, the control unit 140 may control a plurality of images for the 4-chamber view, which are obtained by splitting ultrasound volume data by the image processing unit 120, to be displayed again. Then, the storage unit 110 may store a new image for the 4-chamber view, based on the external input signal.

Alternatively, the control unit 140 may control not only data stored for the observation operation but also data stored for a reference point and an observation plane, to be changed. Specifically, the control unit 140 may control the image processing unit 120 to determine a new reference point and a new observation plane. According to another embodiment of the present invention, the control unit 140 may control images stored to match all observation operations other than images stored to match one observation operation, to be determined again.

Referring to FIG. 10, similar to the process of FIG. 9, the display unit 130 may display observation operations 1, 2, and 3 on a first region 1010, and images 1011, 1012, and 1013 stored to correspond to the observation operations 1, 2, and 3.

Referring to FIG. 9, the images 911, 912, 913, and 914 stored to correspond to the observation operations 1, 2, 3, and 4 are images of A-planes that horizontally split ultrasound volume data, whereas referring to FIG. 10, the images 1011, 112, and 1013 stored to correspond to the observation operations 1, 2, and 3 are images of B-planes or C-planes that vertically split ultrasound volume data.

According to an embodiment of the present invention, as illustrated in FIGS. 9 and 10, the display unit 130 displays observation operations and images corresponding thereto, based on whether each of the observation planes corresponding to these images is an A-plane, a B-plane, or a C-plane. That is, the display unit 130 may display the images stored to correspond to the observation operations such that the images may be classified according to observation planes.

The methods described above may be embodied as a computer program. The computer program may be stored in a computer-readable recording medium, and executed using a general digital computer. Data structures employed in the methods may be recorded on a computer-readable recording medium via various means. Devices that may be used to store programs including computer codes for performing various methods according to the present invention should not be understood as including temporary objects, such as carrier waves or signals. Examples of the computer-readable medium may include a magnetic recording medium (a ROM, a floppy disc, a hard disc, etc.), and an optical recording medium (a CD-ROM, a DVD, etc.).

There are cases where a conventional ultrasound apparatus cannot efficiently diagnose an object, according to the skill level of a user. In particular, in the case of an object, the location and direction of which are irregular, e.g., a fetal heart, a result of diagnosing the object may often vary according to users. However, according to the above embodiments, a user may be automatically provided an image for an observation operation from ultrasound volume data. Accordingly, the object may be efficiently and conveniently diagnosed through an ultrasound examination.

As described above, a user may easily obtain and interpret an ultrasound image of a fetal heart without cumbersome manipulations. Also, even inexperienced users are capable of efficiently obtaining an ultrasound image according to a predetermined protocol. That is, when an ultrasound image of an object, e.g., a fetal heart, is obtained and the object is diagnosed based on the ultrasound image, dependence upon a user and a rate of success may be improved.

While the present invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A method of managing an ultrasound image, the method comprising:
    determining a reference point, an observation plane and a split method of ultrasound volume data according to a current observation operation which is one of a plurality of observation operations for observing a plurality of views of an object;
    obtaining a plurality of images by splitting the ultrasound volume data according to the split method, based on the reference point and the observation plane; and
    storing an image selected from among the plurality of images according to an external input signal such that the selected image matches the current observation operation.

2. The method of claim 1, wherein the obtaining of the plurality of images comprises obtaining the plurality of images by splitting the ultrasound volume data such that planes that split the ultrasound volume data form a predetermined angle with the observation plane.

3. The method of claim 1, wherein the obtaining of the plurality of images comprises obtaining the plurality of images by splitting the ultrasound volume data such that planes that split the ultrasound volume data intersect with respect to the reference point.

4. The method of claim 1, wherein the obtaining of the plurality of images comprises obtaining the plurality of images by adjusting at least one of distances between and a total number of planes that split the ultrasound volume data.

5. The method of claim 1, wherein the observation plane is one of an A-plane, a B-plane, and a C-plane of the object, included in the ultrasound volume data.

6. The method of claim 1, wherein the storing of the image selected from among the plurality of images comprises storing location information of planes that split the ultrasound volume data, together with the selected image, so as to obtain the selected image.

7. The method of claim 1, further comprising displaying the current observation operation and an image stored to match the current observation operation together.

8. The method of claim 7, wherein the displaying of the current observation operation and the image stored to match the current observation operation together comprises displaying an exemplary image of the current observation operation.

9. The method of claim 1, further comprising arranging the ultrasound volume data such that a reference region, including the reference point, is disposed in a determined direction.

10. The method of claim 1, further comprising selecting the current observation operation from among the plurality of observation operations,
    wherein the selecting of the current observation operation comprises selecting the current observation operation from among the plurality of observation operations, according to a predetermined order or an external input signal.

11. The method of claim 1, further comprising selecting one of the plurality of observation operations as a new current observation operation, and
    wherein the method is repeatedly performed.

12. A method of displaying an ultrasound image, the method comprising:
    displaying an order of a current observation operation which is one of a plurality of observation operations for observing a plurality of views of an object, on a first region of a screen;
    displaying at least one of an observation plane, a reference point, and a split method of splitting ultrasound volume data, on a second region of the screen, wherein the observation plane, the reference point, and the split method are determined according to the current observation operation; and
    displaying a plurality of images of planes that split the ultrasound volume data according to the split method based on the observation plane and the reference point, on a third region of the screen.

13. The method of claim 12, wherein the current observation operation is selected from among the plurality of observation operations, according to a predetermined order or an external input signal.

14. The method of claim 12, further comprising marking an image, which is selected from among the plurality of images according to an external input signal, on the third region such that the selected image is differentiated from the other images.

15. An ultrasound apparatus comprising:
a storage unit for storing ultrasound volume data;
an image processing unit for determining a reference point, an observation plane and a split method for the ultrasound volume data according to a current observation operation which is one of a plurality of observation operations for observing, a plurality of views of an object, and obtaining a plurality of images by splitting the ultrasound volume data according to the split method, based on the reference point and the observation plane;
a display unit for displaying the plurality of images; and
a control unit for controlling the storage unit, the image processing unit, and the display unit,
wherein the storage unit stores an image selected from among the plurality of images according to an external input signal such that the selected image matches the current observation operation.

16. The ultrasound apparatus of claim 15, wherein the image processing unit obtains the plurality of images by splitting the ultrasound volume data such that planes that split the ultrasound volume data form a predetermined angle with the observation plane.

17. The ultrasound apparatus of claim 15, wherein the image processing unit obtains the plurality of images by splitting the ultrasound volume data such that planes that split the ultrasound volume data intersect with respect to the reference point.

18. The ultrasound apparatus of claim 15, wherein the image processing unit obtains the plurality of images by adjusting at least one of distances between and a total number of planes that split the ultrasound volume data.

19. The ultrasound apparatus of claim 15, wherein the storage unit stores the selected image together with location information of planes that split the ultrasound volume data, so as to obtain the selected image.

20. The ultrasound apparatus of claim 15, wherein the display unit displays the current observation operation and an image stored to match the current observation operation together.

21. The ultrasound apparatus of claim 20, wherein the display unit displays an exemplary image of the current observation operation.

22. The ultrasound apparatus of claim 15, wherein the image processing unit arranges the ultrasound volume data such that a reference region, including the reference point, is disposed in a determined direction.

23. The ultrasound apparatus of claim 15, wherein the control unit selects the current observation operation from among the plurality of observation operations, according to a predetermined order or an external input signal.

24. The ultrasound apparatus of claim 15, wherein the control unit controls the storage unit, the image processing unit, and the display unit to repeatedly perform a process of determining one of the plurality of observation operations as a new current observation operation and storing an image to match the new current observation operation.

25. An apparatus for displaying an ultrasound image, the apparatus comprising:
an observation operation display module for displaying an order of a current observation operation which is one of a plurality of observation operations for observing a plurality of views of an object, on a first region of a screen;
a split information display module for displaying at least one of an observation plane, a reference point, and a split method of splitting ultrasound volume data, on a second region of the screen, wherein the observation plane, the reference point, and the split method are determined according to the current observation operation; and
a split screen display module for displaying a plurality of images of planes that split the ultrasound volume data according to the split method based on the observation plane and the reference point, on a third region of the screen.

26. The apparatus of claim 25, wherein the current observation operation is selected from among the plurality of observation operations, according to a predetermined order or an external input signal.

27. A method of managing an ultrasound image, the method comprising:
storing a plurality of pieces of setting information to respectively match a plurality of observation operations for observing a plurality of views of an object, each of the plurality of pieces of setting information including information about an observation plane that splits ultrasound volume data in a predetermined direction, information about a split method of splitting the ultrasound volume data, and information about a reference point;
displaying a plurality of plane images for a current observation operation which is one of the plurality of observation operations, wherein the plurality of plane images are obtained by splitting the ultrasound volume data according to the split method, based on the reference point and the observation plane based on a piece of the setting information matching the current observation operation;
storing an image selected from among the plurality of plane images according to an external input signal such that the selected image matches the current observation operation; and
repeatedly performing a process of displaying a new observation operation and storing an image to match the new observation operation.

28. A non-transitory computer-readable recording medium having recorded thereon a computer program for executing the method of claim 1.

29. A non-transitory computer-readable recording medium having recorded thereon a computer program for executing the method of claim 27.

* * * * *